(12) United States Patent
Sterzinger et al.

(10) Patent No.: US 8,574,545 B2
(45) Date of Patent: Nov. 5, 2013

(54) LABELED IODINATED TROPANE FORMULATION

(75) Inventors: Chris Sterzinger, Vancouver (CA); Cara Ferreira, Vancouver (CA); David Leyh, Vancouver (CA); Richard Thorn, Boston, MA (US)

(73) Assignee: Alseres Pharmaceuticals, Inc., Hopkinton, MA (US)

( * ) Notice: Subject to any disclaimer, the term of this patent is extended or adjusted under 35 U.S.C. 154(b) by 675 days.

(21) Appl. No.: 12/409,572

(22) Filed: Mar. 24, 2009

(65) Prior Publication Data

US 2009/0297446 A1 Dec. 3, 2009

Related U.S. Application Data

(63) Continuation-in-part of application No. PCT/CA2008/001916, filed on Oct. 31, 2008.

(60) Provisional application No. 60/984,163, filed on Oct. 31, 2007.

(51) Int. Cl.
*A61K 51/00* (2006.01)
*C07D 451/00* (2006.01)

(52) U.S. Cl.
USPC .......................................... 424/1.85; 546/132

(58) Field of Classification Search
None
See application file for complete search history.

(56) References Cited

U.S. PATENT DOCUMENTS

| | | |
|---|---|---|
| 5,310,912 A | 5/1994 | Neumeyer et al. |
| 5,439,666 A | 8/1995 | Neumeyer et al. |
| 5,493,026 A | 2/1996 | Elmaleh et al. |
| 5,506,359 A | 4/1996 | Madras et al. |
| 5,698,179 A | 12/1997 | Neumeyer et al. |
| 5,750,089 A | 5/1998 | Neumeyer et al. |
| 5,770,180 A | 6/1998 | Madras et al. |
| 5,853,696 A | 12/1998 | Elmaleh et al. |
| 5,948,933 A | 9/1999 | Meltzer et al. |
| 5,980,860 A | 11/1999 | Kung et al. |
| 6,171,576 B1 | 1/2001 | Meltzer et al. |
| 6,180,083 B1 | 1/2001 | Mauclaire et al. |
| 6,241,963 B1 | 6/2001 | Kung et al. |
| 6,447,747 B1 | 9/2002 | Pirotte et al. |
| 6,537,522 B1 | 3/2003 | Neumeyer et al. |
| 6,548,041 B1 | 4/2003 | Meltzer et al. |
| 7,081,238 B2 | 7/2006 | Madras et al. |
| 2002/0159949 A1* | 10/2002 | Madras et al. ............... 424/1.65 |

OTHER PUBLICATIONS

Hettiarachchi et al, Analysis of 2β-carbomethoxy-3β-(4-fluorophenyl)-N-(3-iodo-E-allyl) Nortropane in Rat Plasma, J. Chromatogr. A, vol. 895, Issues 1-2, pp. 87-100 (2000).*
Fischman et al, Rapid Detection of Parkinson's Disease by SPECT With Altropane: A Selective Ligand for Dopamine Transporters, Synapse, vol. 29, Issue 2, pp. 128-141 (1998).*
Fernandez et al, [123I]-Altropane SPECT: How It Compares to Other Positron Emission Tomography and Single-Photon Emission Tomography Dopamine Transporters in Early Parkinson's Disease, Bioimaging in Neurodegeneration, Contemporary Neuroscience, vol. I, pp. 37-44 (2005).*
Cattabeni, F., "Altropane", Current Opinion in Investigational Drugs, PharmaPress Ltd., (2002), 3(11), pp. 1647-1651.
Fischman, A. et al., "[C, 127I] altropane: a highly selective ligand for PET imaging of dopamine transporter sites", Synapse, (2001), 39(4), 332-342.
International Preliminary Report on Patentability in corresponding PCT application No. PCT/CA2008/001916 dated May 14, 2010.

* cited by examiner

*Primary Examiner* — Frederick Krass
*Assistant Examiner* — Dennis J Parad
(74) *Attorney, Agent, or Firm* — Novak Druce Connolly Bove + Quigg LLP

(57) ABSTRACT

A diagnostic formulation is provided comprising a tropane having a radioactive concentration of at least 1.6 mCi/mL at least about 51 hours post creation. The diagnostic formulation optionally comprises a radiolabeled dopamine transporter (DAT) ligand useful in the diagnosis of Parkinson's disease (PS). One example of a radiolabeled dopamine transporter (DAT) ligand example is [$^{123}$I]-2β-carbomethoxy-3β-(4-flurophenyl)-N-(3-iodo-E-allyl) nortropane.

16 Claims, No Drawings

US 8,574,545 B2

LABELED IODINATED TROPANE FORMULATION

RELATED CASE INFORMATION

This application is a continuation-in-part of and claims priority to International Patent Application No. PCT/CA2008/001916, filed Oct. 31, 2008, which claims the benefit of priority under 35 U.S.C. §119(e) to U.S. Ser. No. 60/984,163, filed Oct. 31, 2007, the disclosures of which are incorporated herein by reference in their entirety.

FIELD OF THE INVENTION

This invention is in the field of medicine and in particular diagnostics of neurological disorders. This invention includes a formulation comprising an aqueous solution of [$^{123}$I]-2β-carbomethoxy-3β-(4-flurophenyl)-N-(3-iodo-E-allyl) nortropane, wherein the solution comprises a radioactive concentration of at least about 18 mCi/mL, and particularly about 20 mCi/mL or more.

BACKGROUND OF THE INVENTION

[$^{123}$I]-2β-carbomethoxy-3β-(4-flurophenyl)-N-(3-iodo-E-allyl) nortropane is potentially useful as an aid to diagnosing Parkinson's Syndromes (PS). Without being bound by any particular theory, PS is believed to be characterized by the loss of dopamine-producing neurons in the brain. The loss of dopamine-producing neurons is believed to begin long before symptoms of the disease actually present. Symptoms of PS are often similar to many other movement disorders. Consequently, misdiagnosis rates are high, with some reports of up to 50% misdiagnosis in the early stages. There is currently no available test that can clearly identify Parkinson's Syndromes, especially in early cases. A diagnostic for early stage PS has long been sought.

Without being bound by any particular theory, the dopamine transporter (DAT) is believed to play a significant role in physiological, pharmacological and pathological processes in the brain. The transport system is a primary mechanism for terminating the effects of synaptic dopamine, thereby contributing to the maintenance of homeostasis in dopamine systems. It has also been reported to be a principal target of cocaine in the brain. (Kennedy and Hanbauer, *J. Neurochem.* 1983, 41, 172 178; Shoemaker et al., *Naunyn-Schmeideberg's Arch. Pharmacol.* 1985, 329, 227 235; Reith et al., *Biochem Pharmacol.* 1986, 35, 1123 1129; Ritz et al., *Science* 1987, 237, 1219 1223; Madras et al., *J. Pharmacol. Exp. Ther.* 1989a, 251, 131 141; Bergman et al., *J. Pharmacol. Exp. Ther.* 1989, 251, 150 155; Madras and Kaufman, *Synapse* 1994, 18, 261 275).

The brain grouping formed by the caudate nucleus and the putamen is called the striatum. It constitutes the major target for the cortical afferents of the basal ganglia. The striatum reportedly has the highest levels of dopamine terminals in the brain. A high density of DAT is localized on dopamine neurons in the striatum and appears to be a marker for a number of physiological and pathological states. For example, in Parkinson's Syndromes, dopamine is severely reduced and the depletion of DAT in the striatum has been an indicator for Parkinson's disease (Schoemaker et al., *Naunyn-Schmeideberg's Arch. Pharmacol.* 1985, 329, 227-235; Kaufman and Madras, *Synapse* 1991, 9, 43-49). Consequently, early or pre-symptomatic diagnosis of Parkinson's Syndromes can be achieved by the quantitative measurement of DAT depletion in the striatum. (Kaufman and Madras, *Synapse* 1991, 9, 43-49). Simple and noninvasive methods of monitoring the DAT are quite important. Depletion could be measured by a noninvasive means such as brain imaging using a scintillation camera system and a suitable imaging agent (Frost et al., *Ann. Neurology* 1993, 34, 423 431; Hantraye et al., *Neuroreport* 1992, 3, 265-268). If possible, imaging of the dopamine transporter would also enable the monitoring of progression of the disease and of reversal of the disease such as with therapies consisting of implants of dopamine neurons or drugs that retard progression of the disease. We believe that a radiopharmaceutical that binds to the DAT might provide important clinical information to assist in the diagnosis and treatment of these various disease states.

The decay of the [$^{123}$I] associated with the compound results in the release of a photon with an energy of 159 KeV. This photon easily (and relatively safely) passes through human tissues and bones and can be detected, often by using a radiation detector array in a Single Photon Emission Computed Tomography (SPECT) camera. With appropriate software an image of the site from which the radiation is emerging can be constructed. The image can be compared to images obtained from subjects without signs of Parkinson's Syndromes. A decrease in emmission is presumptive evidence of a loss of dopamine transporter neurons, and potentially a diagnosis of Parkinson's Syndromes.

An effective imaging agent for the disorders described above will exhibit a specific binding affinity and selectivity for the transporter being targeted. In addition, for imaging agents based on radioactive emission, a minimum level of radioactivity is also pertinent. The level of radioactivity is expressed in three ways, specific activity, the concentration of radioactivity, and the total amount of radioactivity administered. In addition, to be a viable commercial product, the radiochemical yield must be reasonable.

Specific activity, in this context, refers to the proportion of 2β-carbomethoxy-3β-(4-fluorophenyl)-N-(3-iodo-E-allyl) nortropane molecules that have $^{123}$I as opposed to $^{127}$I, the non-radioactive iodine isotope. In order to obtain the maximum amount of signal per bound radiochemical molecule, the radiochemical procedure needs to be free of non-radioactive sodium iodide. In radiolabeling 2β-carbomethoxy-3β-(4-flurophenyl)-N-(3-tributyltin-E-allyl) nortropane with $^{123}$I-sodium iodide, the chemical amount of $^{123}$I is extremely small relative to the amounts found in ordinary chemical reactions. Special expertise and experience are generally required to achieve high-yield radio-labeling reaction conditions, and optimizing the conditions requires experimentation. In addition the optimization of the process is particularly expensive at large scale and requires special precautions due to the large amounts of radioactivity.

The concentration of the radiochemical and its stability are key factors in the successful commercial viability of radiochemicals. The radiochemical and chemical stability of each uniquely structured radio-labeled entity is unpredictable from the structure alone. Furthermore, the effect of additives meant to increase stability cannot be known in advance of experimental testing. In addition, for those compounds with short half-life isotopes such as the one discussed herein, the shelf life is usually directly related to the concentration of the product. So long as the compound is stable to the effects of the additional radiation, the shelf life can be extended by using a higher the concentration of the compound. In this regard, [$^{123}$I]2β-carbomethoxy-3β-(4-flurophenyl)-N-(3-iodo-E-allyl) nortropane may be more useful if it can be produced in sufficiently high concentrations such that it would still be emitting at suitable levels for a longer useful period of time. Periods for detectable emissions of one or two days, or longer, after creation are noted.

SUMMARY OF THE INVENTION

In one aspect, the invention features a diagnostic formulation comprising an aqueous solution comprising [$^{123}$I]-2β-carbomethoxy-3β-(4-flurophenyl)-N-(3-iodo-E-allyl) nortropane.

In one embodiment the formulation comprises a radioactive concentration of at least about 18-20 mCi/mL. In another embodiment, the formulation exhibits radioactive concentration of at least about 1.6 mCi/mL at least about 51 hours post-creation. In yet another embodiment the formulation comprises a pH of less than about 7. In another embodiment the formulation comprises a radiochemical purity of at least about 95%. In another embodiment the formulation comprises a concentration of ethanol in a percentage of less than about 10%. In another embodiment the formulation is substantially carrier free. In another embodiment the formulation is substantially ascorbic acid free.

In another aspect, the invention features a method of preparing [$^{123}$I]-2β-carbomethoxy-3β-(4-flurophenyl)-N-(3-iodo-E-allyl) nortropane comprising the steps of: a) Preparing a precursor solution comprising 2β-Carbomethoxy-3β-(4-fluorophenyl)-N-(3-tributyltin-E-allyl) nortropane), ethanol, hydrogen peroxide, and phosphate buffer; b) Preparing a sodium [$^{123}$I]-iodide solution comprising sodium [$^{123}$I]-iodide and trifluoroacetic acid having a pH of less than about 2; and c) Heating a mixture of precursor solution and sodium [$^{123}$I]-iodide solution at a temperature of about 80° C. for about 15 minutes.

In another aspect, the invention features a method of preparing an aqueous solution of [$^{123}$I]-2β-carbomethoxy-3β-(4-flurophenyl)-N-(3-iodo-E-allyl) nortropane comprising the steps of: eluting the [$^{123}$I]-2β-carbomethoxy-3β-(4-flurophenyl)-N-(3-iodo-E-allyl) nortropane through a C18 preparative HPLC column with an eluent, wherein the eluent comprises about 15% (v/v) ethanol; and Collecting the product peak in sodium chloride in an acetic acid buffer; wherein the radioactive concentration of the resulting solution is at least about 23 mCi/mL.

In another aspect, the invention features a product formed by the process for producing [$^{123}$I]-2β-carbomethoxy-3β-(4-flurophenyl)-N-(3-iodo-E-allyl) nortropane.

DETAILED DESCRIPTION OF THE INVENTION

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

For commercial production, it is important to maximize radiolabel (e.g. $^{123}$I) incorporation into a final product as well as minimize the reaction time. It is also required for safety of use that the final product has radiochemical and chemical purity acceptable to national regulatory agencies. Furthermore, since neither of the initial reactants is stable at low pH but the iodination reaction is optimal at low pH, care is taken to employ a process whereby the reaction period under acidic conditions is minimized.

The successful commercialization of the product is further enhanced if the shelf life/stability can be lengthened. One method by which this can be accomplished is by increasing the final product's radioactive concentration. Since a radiolabel such as $^{123}$I has a half life of only 13.2 hours, extending the shelf life by an additional day suggests that the initial level of radioactivity should be increased about four-fold. Increased concentrations of radioactivity potentially reduce the stability of the product because of direct effects of radiation on the compound and by indirect effects caused by the generation of highly reactive compounds, including highly reactive compounds, from water. A more useful compound is one with the highest concentration of radioactive compound (s) that maintains sufficient chemical and radiochemical stability for the duration of use.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "carrier" is used herein to mean a non-radioactive version of a compound.

The term "radiochemical yield" is the percentage of radioactive compound incorporated into a final product.

Tropane is a bicyclic tertiary amine compound $C_8H_{15}N$ that is the parent compound of atropine, cocaine, and related alkaloids. Certain small organic molecules, some of which have high affinity and selectivity for the dopamine transporter (DAT), and are useful in the diagnosis of Parkinson's disease (PS).

In one embodiment the tropane compound as disclosed in U.S. Pat. No. 5,493,026. In one embodiment, the tropane compound is [$^{123}$I]-2β-carbomethoxy-3β-(4-flurophenyl)-N-(3-iodo-E-allyl) nortropane. It is believed that, when given intravenously, [$^{123}$I]-2β-carbomethoxy-3β-(4-flurophenyl)-N-(3-iodo-E-allyl) nortropane (Altropane®, Alseres Pharmaceuticals, Inc. Hopkinton, Mass.) is able to penetrate the brain and bind to dopamine transport receptors.

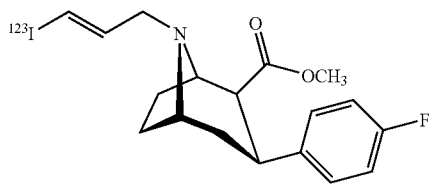

[$^{123}$I]-2β-carbomethoxy-3β-(4-flurophenyl)-N-(3-iodo-E-allyl) nortropane

Other examples of imaging agents that target the dopamine transporter include [$^{123}$I] N-ω-fluoropropyl-2β-carbomethoxy-3β-(4-iodophenyl) nortropane or Ioflupane ($^{123}$I) (DaTSCAN™, Nycomed-Amersham, Piscataway, N.J.), PE2I ($^{11}$C or $^{18}$F), (−)-2-β-Carbomethoxy-3-β-(4-fluorophenyl)tropane (β-CFT, WIN 35,428), ($^{99m}$Tc) 0-1505, and ($^{99m}$Tc)-Technepine. The above agents and other examples of useful DAT ligands include but are not limited to compounds disclosed in Fischman et al., 1998, *Synapse*, 29:125-41, Madras et al., 1996, *Synapse* 22:239-46; Meltzer et al., 1993, *J. Med. Chem.* 36:855-62; and Milius et al., 1990, *J. Medicinal Chem.* 34:1728-31, U.S. Pat. Nos. 5,493,026; 5,506,359; 5,770,180; 5,853,696; 5,948,933; 6,171,576; 6,548,041; 7,081,238; 6,180,083; 5,310,912; 5,439,666; 5,698,179; 5,750,089; 6,447,747; 6,537,522; 5,980,860; 6,241,963 and 6,180,083.

In one aspect, the invention features a diagnostic formulation comprising an aqueous solution comprising [$^{123}$I]-2β-carbomethoxy-3β-(4-flurophenyl)-N-(3-iodo-E-allyl) nortropane, optionally wherein the aqueous solution is substantially carrier-free and substantially ascorbic acid-free.

In another embodiment, the aqueous solution is substantially radioprotectant-free.

In one embodiment, the aqueous solution comprises a radioactive concentration of at least about 15 and 18, and about 20 mCi/mL or more. In another embodiment, the aqueous solution comprises a radioactive concentration of at least about 23 mCi/mL.

In another embodiment, the aqueous solution comprises a radioactive concentration of at least about 1.6 mCi/mL at least about 50 hours post creation.

In one embodiment, the aqueous solution has a radiochemical purity of at least about 95%, and particularly at least about 97%.

In another embodiment, the aqueous solution comprises a concentration of ethanol in a percentage of less than about 10%, and less than about 5%, and further less than about 1%. In another embodiment, the aqueous solution is substantially ethanol-free.

In another embodiment, the aqueous solution comprises a pH of less than about 7. In another embodiment, the aqueous solution comprises a pH of less than about 6. In another embodiment, the aqueous solution comprises a pH ranging from about 2.5 to about 4.5.

In one embodiment, the [$^{123}$I]-2β-carbomethoxy-3β-(4-fluophenyl)-N-(3-iodo-E-allyl) nortropane is stable for at least 48 hours. In another embodiment, the [$^{123}$I]-2β-carbomethoxy-3β-(4-fluorophenyl)-N-(3-iodo-E-allyl) nortropane is stable for at least about 60 hours.

In another aspect, the invention features a process for producing [$^{123}$I]-2β-carbomethoxy-3β-(4-fluorophenyl)-N-(3-iodo-E-allyl) nortropane. In one embodiment the process comprises the reaction of 2β-Carbomethoxy-3β-(4-fluorophenyl)-N-(3-tributyltin-E-allyl) nortropane and sodium [$^{123}$I]-iodide. In another embodiment the process produces [$^{123}$I]-2β-carbomethoxy-3β-(4-fluorophenyl)-N-(3-iodo-E-allyl) nortropane in less than about 60 minutes, with greater than 95% radiochemical purity, a concentration of at least about 20 mCi/mL, a radiochemical yield of at least about 45% (and particularly at least about 65%, and at least about 75%), without added carrier, and having a radiochemical and chemical stability sufficient for over about 50 hours, and particularly at least about 51 hours.

In another aspect, the invention features a process for producing an aqueous solution of [$^{123}$I]-2β-carbomethoxy-3β-(4-fluorophenyl)-N-(3-iodo-E-allyl) nortropane. In one embodiment, the solution is produced using a process comprising purification using hydrophobic media that allows separation and concentration. In another embodiment, a Preparative HPLC purification. In one embodiment, the purification step is substantially free of a radiolysis inhibitor. In another embodiment, the purification step comprises the addition of a radiolysis inhibitor. In another embodiment, the purification step of the target compound is performed within 30 minutes.

Any suitable preparative HPLC system may be used but note is made of an HPLC column comprising packing material particles having an 18 carbon chain (C18). Examples of C18 columns include but are not limited to XTerra® C18 Column, (Waters Corp., Milford, Mass., See U.S. Pat. No. 6,686,035), and µBondpak C18 Column (Waters Corp., Milford, Mass.).

In one embodiment the process for producing [$^{123}$I]-2β-carbomethoxy-3β-(4-fluorophenyl)-N-(3-iodo-E-allyl) nortropane comprises the steps of:
a) Heating a basic solution (pH at least about 11) of sodium [$^{123}$I]-iodide to a range of about 70° C. to about 150° C.
b) Separately combining 2β-Carbomethoxy-3β-(4-fluorophenyl)-N-(3-tributyltin-E-allyl) nortropane in great molar excess (about 0.05 to about 0.5 mg) in ethanol, an oxidizing agent (e.g., H$_2$O$_2$), and a buffer (e.g. sodium phosphate) at about pH 2.5 to 3.0
c) Acidifying the heated sodium [$^{123}$I]-iodide to a pH less than about 2 using an appropriate buffer (e.g. trifluoroacetic acid) and adding the mixture defined in step (b)
d) Heating the mixture from (c) for about 20 minutes or less at a temperature ranging from about 70° C. to about 150° C.
e) Neutralizing the pH (e.g., by adding base such as NaOH) and an oxidizing agent (e.g. sodium metabisulfite)
f) Purifying the [$^{123}$I]-2β-carbomethoxy-3β-(4-fluorophenyl)-N-(3-iodo-E-allyl) nortropane reaction product using hydrophobic media that allows separation and concentration (with or without radiolysis inhibitors) of the target compound within about 30 min, and
g) Diluting into an isotonic saline solution with acidic (less than about pH 7) buffer (e.g. phosphate) with or without radiolysis inhibitors (e.g. ascorbic acid) to a concentration of about 23 mCi/mL.
h) Sterilizing by autoclaving if the formulation buffer is less than about pH 6 (optionally pH about 2.5 to about 4.5), Optionally the solution at pH about 2.5 to about 7.0 may be sterilized by filtration (note: any lower limitation on useful pH is a function of degree of injection discomfort and not due to chemical instability).

In another aspect, the invention features a product formed by the process for producing [$^{123}$I]-2β-carbomethoxy-3β-(4-fluorophenyl)-N-(3-iodo-E-allyl) nortropane. In one embodiment the product formed by the process of preparing a precursor solution comprising 2β-Carbomethoxy-3β-(4-fluorophenyl)-N-(3-tributyltin-E-allyl) nortropane, ethanol, hydrogen peroxide, and phosphate buffer; preparing a sodium [$^{123}$I]-iodide solution comprising sodium [$^{123}$I]-iodide and trifluoroacetic acid having a pH of less than about 2; heating a mixture of precursor solution and sodium [$^{123}$I]-iodide solution at a temperature of about 80° C. for about 15 minutes; eluting the [$^{123}$I]-2β-carbomethoxy-3β-(4-fluorophenyl)-N-(3-iodo-E-allyl) nortropane through a C18 preparative HPLC column with an eluent, wherein the eluent comprises about 15% (v/v) ethanol; and collecting the product peak in sodium chloride in an acetic acid buffer.

EXAMPLES

Example 1

Synthesis of [$^{123}$I]-2β-carbomethoxy-3β-(4-fluorophenyl)-N-(3-iodo-E-allyl) nortropane Sodium [$^{123}$I]-iodide (4 Ci) in 0.1N NaOH was dispensed in a 10 mL vial and heated to about 80° C. Phosphate buffer, 0.80 mL 0.1 M, pH 2.5-3.0, was combined with 0.20 mL 30% hydrogen peroxide, and 0.50 mL of 1 mg/mL (in ethanol) 2β-Carbomethoxy-3β-(4-fluorophenyl)-N-(3-tributyltin-E-allyl) nortropane) to form a precursor containing mixture. The sodium [$^{123}$I]-iodide solution was acidified (final pH <2) by the addition of Trifluoroacetic acid. The precursor-containing mixture was added to the acidified sodium [$^{123}$I]-iodide solution. The mixture was heated at 80° C. for 15 minutes.

After 15 minutes, 2 mL of sodium metabisulfite solution was added to stop the reaction (100 mg/mL in Sterile Water for Injection). One mL of a 100 mg/mL solution of Ascorbic Acid was added to the reaction mixture as a radioprotectant. The acidic reaction mixture is optionally neutralized with 500 μL of 5 N Sodium Hydroxide. After neutralization, the pH is >6. Neutralization may be optional if the subsequent HPLC system is not degraded too quickly by the low pH and oxidant.

Example 2

Chromatography of [$^{123}$I]-2β-carbomethoxy-3β-(4-flurophenyl)-N-(3-iodo-E-allyl) nortropane The reaction mixture of Example 1 was transferred to a preparative HPLC system (XTerra® C18 Column from Waters Corp., Milford, Mass., see U.S. Pat. No. 6,686,035).

| XTerra ® column | |
| --- | --- |
| Packing Material: | C-18 |
| Particle Size: | 5 μm |
| Length: | 50 mm |
| Diameter: | 10 mm |
| Column Volume: | 4 mL |

[$^{123}$I]-2β-carbomethoxy-3β-(4-flurophenyl)-N-(3-iodo-E-allyl) nortropane was eluted using the following eluent system: isocratic elution buffer, 15% (v/v) ethanol, 85% 10 mM glacial acetic acid in sterile water for injection. The product peak was collected into a vessel containing sodium chloride injection (USP) in an acetic acid buffer pH 2.5 to 3.5, and, due to carry over, the final solution has about 1.8% ethanol. Noted is the fact that in particular embodiments, the product comprises an aqueous solution comprising 0.1-5 mCi/mL, at the time of production, [$^{123}$I]-2β-carbomethoxy-3β-(4-flurophenyl)-N-(3-iodo-E-allyl) nortropane, 3.5-10% ethanol, 0.2-0.4 mg/mL ascorbic acid, 5-50 μM glacial acetic acid, sodium hydroxide buffer, pH 2.5-3.5, and 0.85-0.95% sodium chloride. Also noted are embodiments wherein the product comprises an aqueous solution comprising 0.1-23 mCi/mL, at the time of production, [$^{123}$I]-2β-carbomethoxy-3β-(4-flurophenyl)-N-(3-iodo-E-allyl) nortropane, 1.5-10% ethanol, 0-0.4 mg/mL ascorbic acid, 5-50 μM glacial acetic acid, sodium hydroxide buffer, pH 2.5-3.5, and 0.85-0.95% sodium chloride. The instant resulting radioactive concentration of [$^{123}$I]-2β-carbomethoxy-3β-(4-fluorophenyl)-N-(3-iodo-E-allyl) nortropane was about 23 mCi/mL.

Example 3

Chromatography of [$^{123}$I]-2β-carbomethoxy-3β-(4-flurophenyl)-N-(3-iodo-E-allyl) nortropane The reaction mixture of Example 1 was transferred to a preparative HPLC system (μBondpak® C18 Column from Waters Corp., Milford, Mass.).

| μBondpak column | |
| --- | --- |
| Packing Material: | C-18 |
| Particle Size: | 10 μm |
| Length: | 300 mm |
| Diameter: | 19 mm |
| Column Volume: | 85 mL |

[$^{123}$I]-2β-carbomethoxy-3β-(4-flurophenyl)-N-(3-iodo-E-allyl) nortropane was eluted using the following eluent system: isocratic elution buffer, 80% (v/v) ethanol, 20% ascorbic acid in sterile water for injection 20 g/L. The product peak was collected into a vessel containing sodium chloride injection (USP) in an acetic acid buffer pH 2.5 to 3.5. Due to carry over the final solution has about 3.8 to about 6.3% ethanol and about 0.2 to about 0.4 g/L ascorbic acid. The resulting radioactive concentration of [$^{123}$I]-2β-carbomethoxy-3β-(4-flurophenyl)-N-(3-iodo-E-allyl) nortropane was about 5 mCi/mL of solution.

Example 4

Dilution of [$^{123}$I]-2β-carbomethoxy-3β-(4-flurophenyl)-N-(3-iodo-E-allyl) nortropane The chromatographed mixture of Example 2 is adjusted by dilution with acetic acid buffer, pH 2.5 to 4.5, to produce an aqueous solution comprising 16 mCi/mL, (at the time of production), [$^{123}$I]-2β-carbomethoxy-3β-(4-fluorophenyl)-N-(3-iodo-E-allyl) nortropane, 4% ethanol, 10 μM glacial acetic acid, sodium hydroxide buffer, pH 2.5-3.5, and 0.9% sodium chloride.

Example 5

Dilution of [$^{123}$I]-2β-carbomethoxy-3β-(4-flurophenyl)-N-(3-iodo-E-allyl) nortropane The chromatographed mixture of Example 3 is adjusted by dilution with acetic acid buffer, pH 2.5 to 4.5, to produce an aqueous solution comprising 4 mCi/mL (at the time of production), [$^{123}$I]-2β-carbomethoxy-3β-(4-fluorophenyl)-N-(3-iodo-E-allyl) nortropane, 4% ethanol, 0.3 mg/mL ascorbic acid, 10 μM glacial acetic acid, sodium hydroxide buffer, pH 2.5-3.5, and 0.9% sodium chloride.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A formulation comprising an aqueous solution comprising [$^{123}$I]-2β-carbomethoxy-3β-(4-fluorophenyl)-N-(3-iodo-E-allyl) nortropane, wherein the solution comprises a radioactive concentration of at least about 18 mCi/mL, wherein the [$^{123}$I]-2β-carbomethoxy-3β-(4-fluorophenyl)-N-(3-iodo-E-allyl) nortropane is stable for at least 48 hours.

2. The formulation of claim 1, wherein the radioactive concentration is at least about 23 mCi/mL.

3. A formulation comprising an aqueous solution comprising [$^{123}$I]-2β-carbomethoxy-3β-(4-fluorophenyl)-N-(3-iodo-E-allyl) nortropane, wherein the solution comprises a radioactive concentration of at about 4 mCi/mL, wherein the [$^{123}$I]-2β-carbomethoxy-3β-(4-fluorophenyl)-N-(3-iodo-E-allyl) is stable for at least 48 hours.

4. A formulation comprising an aqueous solution comprising [$^{123}$I]-2β-carbomethoxy-3β-(4-fluorophenyl)-N-(3-iodo-E-allyl) nortropane, wherein the solution comprises a radioactive concentration of at about 16 mCi/mL, wherein the [$^{123}$I]-2β-carbomethoxy-3β-(4-fluorophenyl)-N-(3-iodo-E-allyl) is stable for at least 48 hours.

5. A formulation comprising an aqueous solution comprising [$^{123}$I]-2β-carbomethoxy-3β-(4-fluorophenyl)-N-(3-iodo-E-allyl) nortropane, wherein the formulation exhibits radioactive concentration of at least about 1.6 mCi/mL at least about 51 hours post creation, wherein the [$^{123}$I]-2β-carbomethoxy-3β-(4-fluorophenyl)-N-(3-iodo-E-allyl) is stable for at least 48 hours.

6. The formulation of claim 1, wherein the aqueous solution comprises a pH of less than about 7.

7. The formulation of claim 1, wherein the aqueous solution comprises a pH of less than about 6.

8. The formulation of claim 1, wherein the aqueous solution comprises a pH ranging from about 2.5 to about 4.5.

9. The formulation of claim 1, wherein the aqueous solution comprises a radiochemical purity of at least about 95%.

10. The formulation of claim 1, wherein the aqueous solution comprises a concentration of ethanol of less than about 10% (v/v).

11. The formulation of claim 1, wherein the aqueous solution comprises a concentration of ethanol of less than about 5% (v/v).

12. The formulation of claim 1, wherein the aqueous solution comprises a concentration of ethanol of less than about 1% (v/v).

13. The formulation of claim 1, wherein the aqueous solution is substantially free of ethanol.

14. The formulation of claim 1, wherein the aqueous solution is substantially carrier free.

15. The formulation of claim 1, wherein the aqueous solution is substantially ascorbic acid free.

16. The formulation of claim 1, wherein said [$^{123}$I]-2β-carbomethoxy-3β-(4-fluorophenyl)-N-(3-iodo-E-allyl) nortropane is stable for at least about 60 hours.

* * * * *